United States Patent
Maes et al.

(10) Patent No.: US 6,495,372 B1
(45) Date of Patent: Dec. 17, 2002

(54) FIELD TEST APPARATUS AND METHOD FOR ANALYSIS OF COOLANTS AND HEAT-EXCHANGE FLUIDS

(75) Inventors: Jean-Pierre Maes, Merelbeke (BE); Peter Roose, Sint Martens Latem (BE); Filip Van Kenhove, St. Amands (BE)

(73) Assignee: Texaco Inc., White Plains, NY (US)

(*) Notice: Subject to any disclaimer, the term of this patent is extended or adjusted under 35 U.S.C. 154(b) by 0 days.

(21) Appl. No.: 09/406,057

(22) Filed: Sep. 27, 1999

(30) Foreign Application Priority Data

Sep. 28, 1998 (EP) .............................. 98307868

(51) Int. Cl.[7] .............................................. G01N 31/22
(52) U.S. Cl. .......................... 436/163; 422/75; 422/76; 422/77
(58) Field of Search ............... 436/68, 163; 422/75–77, 422/82.03, 82.05, 92

(56) References Cited

U.S. PATENT DOCUMENTS

| | | | |
|---|---|---|---|
| 3,625,620 A | * 12/1971 | Goldberg | 356/135 |
| 3,717,435 A | * 2/1973 | Ertl et al. | 422/75 |
| 4,209,416 A | * 6/1980 | Hirozawa et al. | 252/76 |
| 4,227,976 A | 10/1980 | Menke | |
| 4,266,942 A | * 5/1981 | Vandenbosshe | 422/76 |
| 4,647,392 A | 3/1987 | Darden et al. | |
| 4,759,864 A | 7/1988 | Van Neste et al. | |
| 4,851,145 A | 7/1989 | Van Neste et al. | |
| 4,859,608 A | * 8/1989 | Frueh | 436/163 |
| 4,999,305 A | * 3/1991 | Wolcott | 436/52 |
| 5,366,651 A | 11/1994 | Maes et al. | |

FOREIGN PATENT DOCUMENTS

| | | |
|---|---|---|
| DE | 715 397 | 2/1942 |
| EP | 0 479 470 | 4/1992 |
| EP | 0 564 721 | 10/1993 |
| EP | 0 573 287 | 12/1993 |
| FR | 2 748 112 | 10/1997 |

OTHER PUBLICATIONS

Cooper and Doran "Analytical Chemistry by Open Learning. Classical Methods", vol. 1, p. 151, 243–257, 1987, Library of Congress.*
Bodner et al., "Chemistry. Structure and Dynamics. Core Text", John Wiley and Sons, 1996, pp. 468, 470.*
Ryan "Effects of temperature on the accuracy of aqueous engine coolant freezing point determination by refractometer",Soc. Automat. Eng. SP 1993, SP–960 (Engine Coolants, Cooling System Materials and Components), 47–54 (Abstract).*

* cited by examiner

Primary Examiner—Jill Warden
Assistant Examiner—Yelena Gakh
(74) Attorney, Agent, or Firm—Michael J. Stimson; Michael J. Bell; Steven R. Ellinwood (57) ABSTRACT

A test method and apparatus for determining the content of carboxylic acid-based corrosion inhibitors in a coolant or heat exchange fluid. The amount of acidic reagent added to the coolant or fluid between two pH equilibrium points is measured to determine the amount of inhibitors. The refractive index can be measured to determine the amount of freezing point depressant.

12 Claims, 6 Drawing Sheets

FIG. 3    Key: ——— Borax
              — · — Silicate

FIG. 4    Key: ♦ V2(pH=3)-V1
              —— Linear (V2(pH=3)-V1)

y = 0.0664x + 0.068
R² = 0.9997

Equilibrium carboxylate-based

FIELD TEST APPARATUS AND METHOD FOR ANALYSIS OF COOLANTS AND HEAT-EXCHANGE FLUIDS

BACKGROUND OF THE INVENTION

1. Field of the Invention

This invention relates to a method and apparatus for testing the quality of engine coolants and heat-exchange fluids. More particularly, this invention relates to a field test, requiring a minimum of operator interaction.

2. Related Art

Recently Organic Acid Technology (OAT) coolants and heat exchange fluids have been introduced commercially, and provide improved corrosion protection and long life. OAT corrosion inhibitor packages in aqueous and glycol concentrates are used in automotive, heavy duty, marine and industrial applications. OAT inhibitors are also used in secondary cooling systems and in a variety of industrial heat exchange fluids. The use of monocarboxylic or dicarboxylic acids, or the salts of such acids, as corrosion inhibitors in antifreeze/coolant and heat-exchange fluid compositions is disclosed for instance in EP-A-0 479 470, -0 564 721 and -0 573 287. Such compositions may also contain a variety of additives for special purposes, such as hydrocarbyl triazoles for corrosion protection of copper and copper alloys (EP-A-0 564 721).

There is a need to check the quality of the coolant solution regularly to ensure problem-free operation. For the development of OAT coolants, organic acids were neutralized with alkali metal hydroxides (preferably sodium hydroxide (NaOH) or potassium hydroxide (KOH)) to obtain the inhibitor salts used in the new organic formulations, see for example, U.S. Pat. Nos. 4,647,392; 4,851,145; and 4,759,864. It was soon realized that an acid titration of an OAT solution could provide information on the total carboxylic acid inhibitor content. U.S. Pat. No. 5,366,651 shows in FIG. 1 some titration curves for combinations of carboxylate inhibitors with an organic pH buffer such as imidazole.

In order to evaluate the OAT coolant quality in the field, the end user needs to be able to check the amount of contamination with other coolants, as well as carboxylate inhibitor content. The present invention provides an improved method and apparatus for field testing and analysis of coolants and heat exchange fluids.

SUMMARY OF THE INVENTION

According to one aspect of the invention, there is provided a test method for determining the content of carboxylic acid-based corrosion inhibitors in a coolant or heat exchange fluid which comprises:

(a) placing a sample comprising a predetermined amount of the material to be tested in a titration vessel, (b) stirring or otherwise agitating the sample while adding an acidic reagent at a constant rate, (c) measuring the pH of the stirred sample while the acidic reagent is added, (d) determining a first equilibrium point (EP1) demonstrated by a first rapid drop in pH, (e) continuing addition of acidic reagent and measuring the pH until a second equilibrium point (EP2), demonstrated by a second rapid drop in pH, is reached, and (f) determining the amount of carboxylic acid-based corrosion inhibitor in the sample from the amount of acidic reagent added between EP1 and EP2.

Other aspects of the invention provide:

A method wherein the content of contaminant in the sample is determined from the amount of acidic reagent required to reach the first equilibrium point.

A method wherein the amount of freezing point depressant in the sample is determined from the refractive index of the sample.

A method wherein the pH is determined by means of a calibrated electrode in the titration vessel.

A method wherein at least one quantity selected from the observed values of pH, the amount of carboxylic acid corrosion inhibitor, the amount of contaminant, the refractive index, and the freezing point of the sample is displayed visually.

According to another aspect of the invention, there is provided an apparatus for conducting a test method as described above which comprises a titration vessel, first and second reservoirs for acidic reagent and waste neutralizing agents respectively, a first pump for transferring acidic reagent from the first reservoir to the titration vessel and a second pump for transferring waste neutralizing agent to the titration vessel from the second reservoir, a stirrer for stirring samples in the titration vessel, a pH electrode in the titration vessel, display means for displaying information determined by tests conducted in the apparatus, and electronic control means for controlling said apparatus.

The present invention is directed towards a field- or laboratory test technique to determine the quality of antifreeze/coolant or aqueous heat-transfer or heat-exchange fluids. An apparatus and method are described by means of which it is possible to measure the content of carboxylate corrosion inhibitors in OAT coolants or heat exchange fluids, such as Havoline Extended Life Coolant (XLC) (Havoline products available from Texaco Inc.), or heat exchange fluids containing Havoline Extended Life Corrosion Inhibitor (XLI) or mixtures thereof. In one preferred aspect of the invention, the method is used to also measure the contamination level in XLC contaminated by traditional borate or phosphate containing coolant or with the more recently introduced hybrid OAT-traditional coolants such as Havoline Antifreeze Coolant (AFC). Alternatively, it is of course possible to make calibrations for other OAT coolants.

In another aspect of the present invention, the measurement of contamination level, carboxylate corrosion inhibitor content is combined with a measurement of the pH of the test solution.

In yet another preferred aspect of the invention, the measurements of contamination level, total carboxylate inhibitor content and pH are combined with a refractometric determination of the freezing point of the test solution.

BRIEF DESCRIPTION OF THE FIGURES

The invention will be further described with reference to the accompanying Drawings in which.

DETAILED DESCRIPTION OF THE PREFERRED EMBODIMENTS

This invention relates to a method and apparatus for testing the quality of engine coolants and heat-exchange fluids containing long life organic corrosion inhibitors, comprising alkali metal, ammonium or amine salts of carboxylic acids. Such coolants are usually referred to as Organic Acid Technology (OAT) coolants or heat-exchange fluids. More particularly, this invention relates to a field test, requiring a minimum of operator interaction optionally determining, separately or combined in one test sequence, values for carboxylate inhibitor content, contamination level, pH and frost protection of the tested coolant or heat-exchange fluid.

The corrosion inhibitors used in engine coolants are inorganic and/or organic compositions which can be considered as chemical bases. Generally a coolant has a pH of approximately 6.5–9.5 in order to ensure adequate protection of the metals used in engines and cooling and heat-exchange systems. Since the corrosion inhibitors are chemical bases, an analytical technique such as an acid-base titration with hydrogen chloride can be used for the determination of the inhibitor concentrations. The pH of the used coolant provides information on further suitability for use. pH values that are too high or too low may be detrimental to some engine- or heat-exchange system materials. Finally, if applicable, a check on the freezing point will provide information on frost protection.

Figure 1:
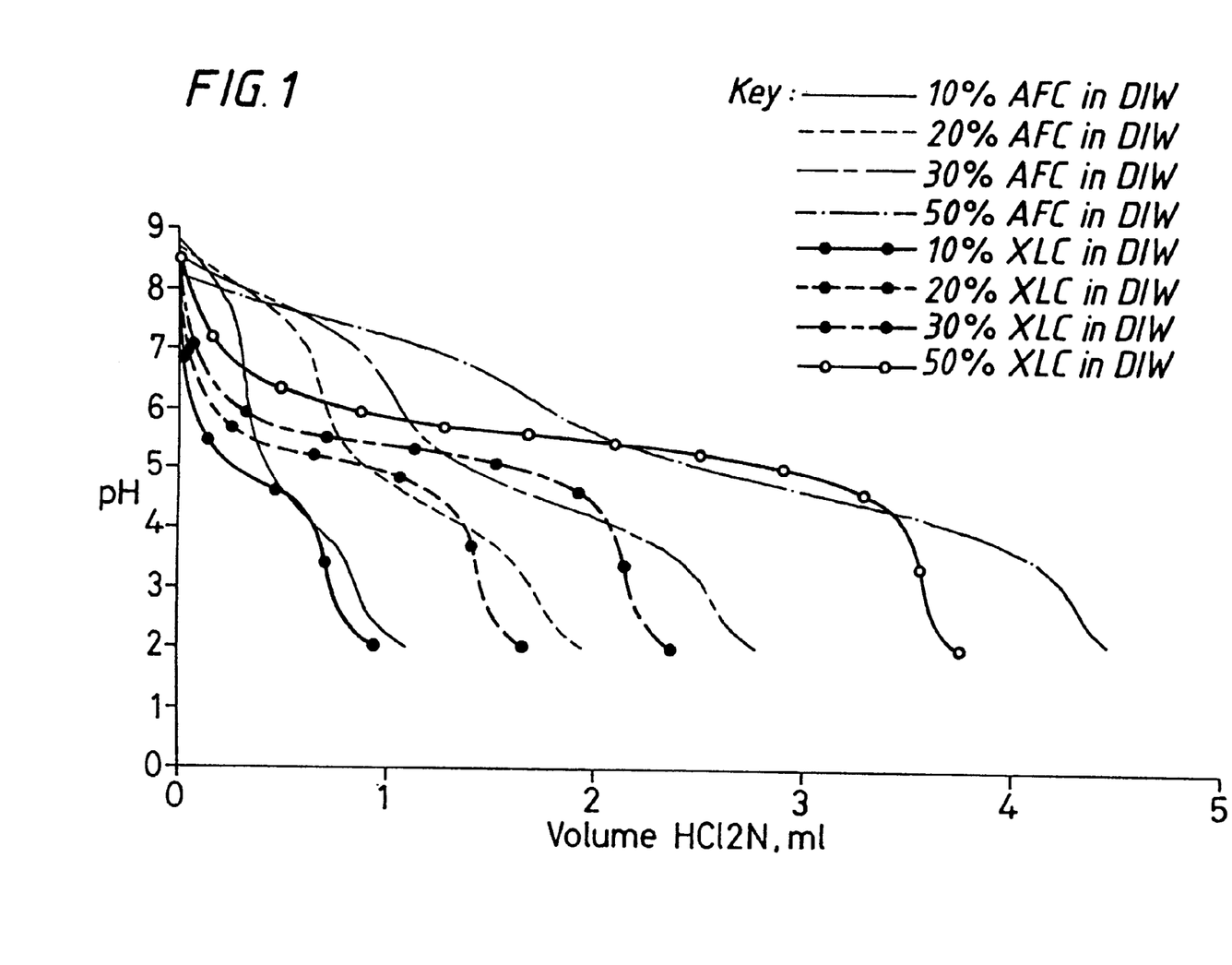
FIG. 1 is a graphical plot showing the effect of the metered addition of acid upon the pH of aqueous solutions (Volume HC12N,ml) of certain commercial OAT coolants.

FIG. 1 shows the difference between the acid-base titration of a hybrid coolant containing borate, silicate and benzoate and carboxylate based inhibitors. These are Havoline Antifreeze Coolant (hereinafter indicated by the abbreviation AFC) and a fully carboxylate based technology Havoline Extended Life Coolant (hereinafter indicated by the abbreviation XLC). FIG. 1 shows the effect upon pH of the addition of 2N hydrochloric acid (HC12N) to eight samples showing various amounts of AFC and XLC in deionized water (DIW). Four curves show respectively 10%, 20%, 30% and 50% AFC in DIW. The other four curves show respectively 10%, 20%, 30% and 50% XLC in DIW.

Figure 2:
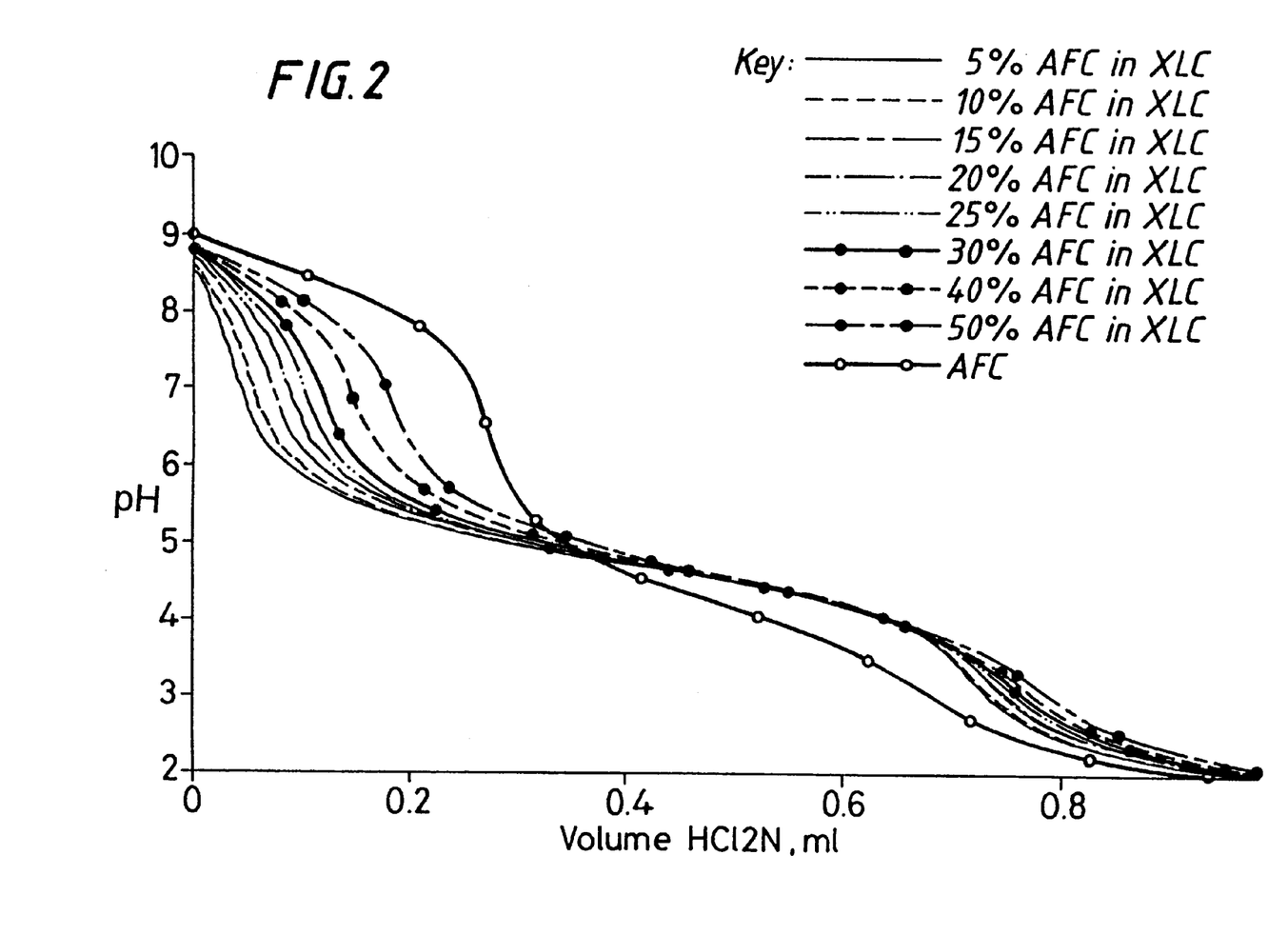
FIG. 2 is a graphical plot showing the effect of the metered addition of acid upon the pH of aqueous solutions (Volume HC12N,ml) of mixtures of commercial OAT coolants.

FIG. 2 shows the effect upon pH of metered addition of 2N hydrochloric acid to different mixtures of AFC and XLC. The curves show respectively 5%, 10%, 15%, 20%, 30%, 40% and 50% of AFC in XLC; one curve shows pure AFC.

Figure 3:
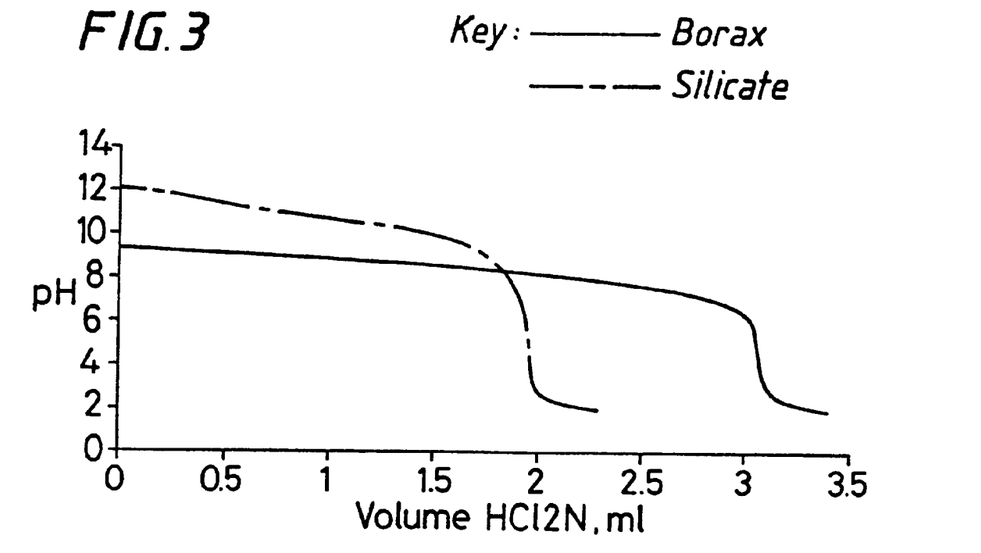
FIG. 3 is a graphical plot showing the effect of the metered addition of acid upon the pH to aqueous solutions (Volume HC12N,ml) of borax and silicate inhibitors.

FIG. 3 shows the effect upon pH of metered addition of 2N hydrochloric acid for solutions of borax and silicate. The influence on the positioning of the first equilibrium point is clearly shown. This makes it possible to evaluate unequivocally the amount of traditional inhibitors in a titrated coolant sample, and consequently the amount of contamination.

In the titration curves of the hybrid coolant with hydrogen chloride, two distinct equilibrium points (EP) can be observed. The titration curve for the carboxylate based, XLC, cooling shows a first equilibrium point (EP1) at approximately pH=7.0, but only a small amount of acid is consumed at this point. This may be compared with the hybrid coolant, AFC, which already shows a considerable consumption of acid at EP1. Up to EP1, all silicate- and borate-based inhibitors are neutralized by the acid. Between EP1 and the second equilibrium point EP2, carboxylates are converted into the corresponding organic acids. This can be also derived from the acid-base dissociation constants for the inhibitors silicate (NaHSiO$_3$ pK$_a$=9.2) and typical aliphatic organic acids (RCOOH pK$_a$=4.5).

These titration curves make it possible to estimate the amount of traditional inhibitors used in a titrated coolant sample, this can be derived from the volume of acid consumed at EP1. In addition, the shape of these titration curves indicated that the amount of carboxylates can be measured from the added acid volume difference between EP1 and EP2.

Experiment has demonstrated a linear correlation between the organic acid concentration used in the Texaco coolant Havoline XLC and the difference between the volume of acid added (in cm$^3$) at the second equilibrium point (V2 at pH 3) and the volume added at the first equilibrium point (V1 at pH 7). This is illustrated below in the Table and graphically in FIG. 4.

TABLE

| % XLC | V1 (cm$^3$) | V2 (cm$^3$) | Measured V2–V1 (cm$^3$) |
|---|---|---|---|
| 10 | 0.0275 | 0.74 | 0.7125 |
| 20 | 0.0545 | 1.46 | 1.4055 |
| 30 | 0.087 | 2.17 | 2.083 |
| 50 | 0.2075 | 3.58 | 3.3725 |

Figure 4:
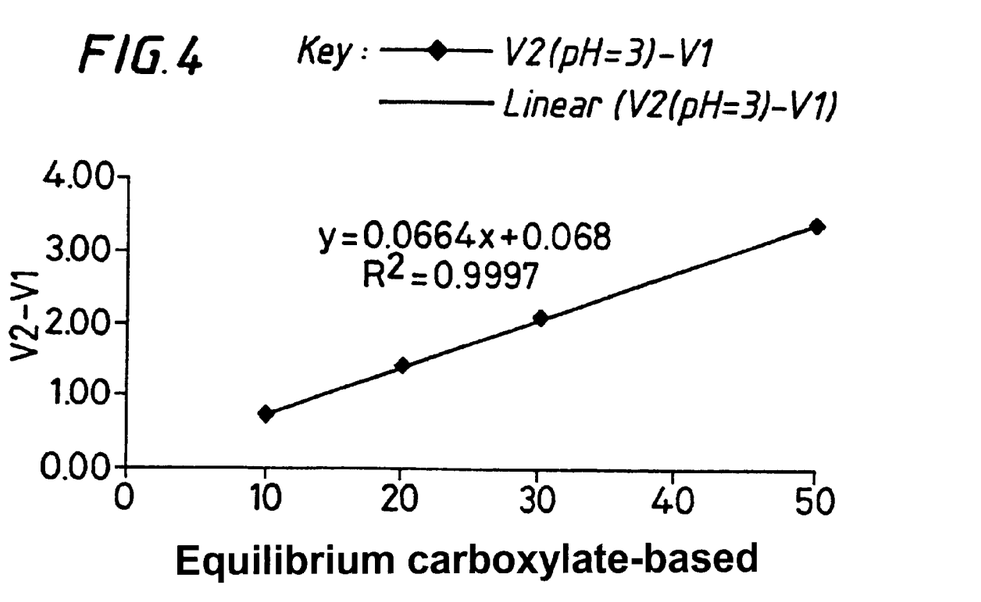
FIG. 4 is a graphical plot of carboxylic acid content ($V_2-V_1$ in $cm^3$) and equilibrium points (percent concentration) for a carboxylic based coolant.

FIG. 4 shows the correlation between the carboxylic acid contents and the measured acid volumes added between the first and second equilibrium points. It will be seen that the data points representing V1–V2 for the four percentage concentrations lie in a straight line.

Figure 6:
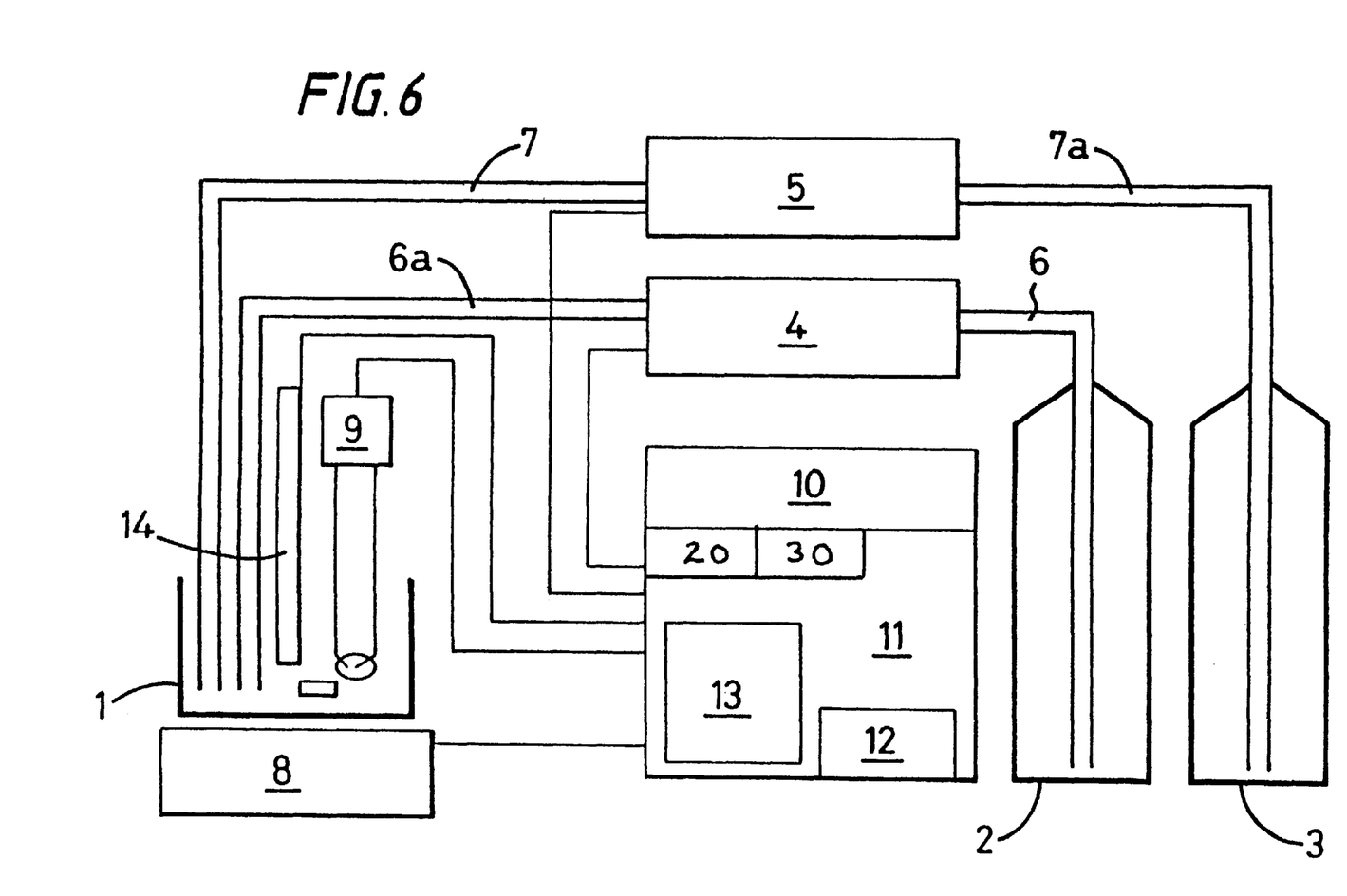
FIG. 6 is a schematic view of one embodiment of apparatus according to the invention.

FIG. 6 shows one possible preferred embodiment (in schematic fashion) of an apparatus according to the invention for measuring the contamination levels in OAT, the total carboxylate content, and optionally, the coolant pH and extent of frost protection.

Figure 7:
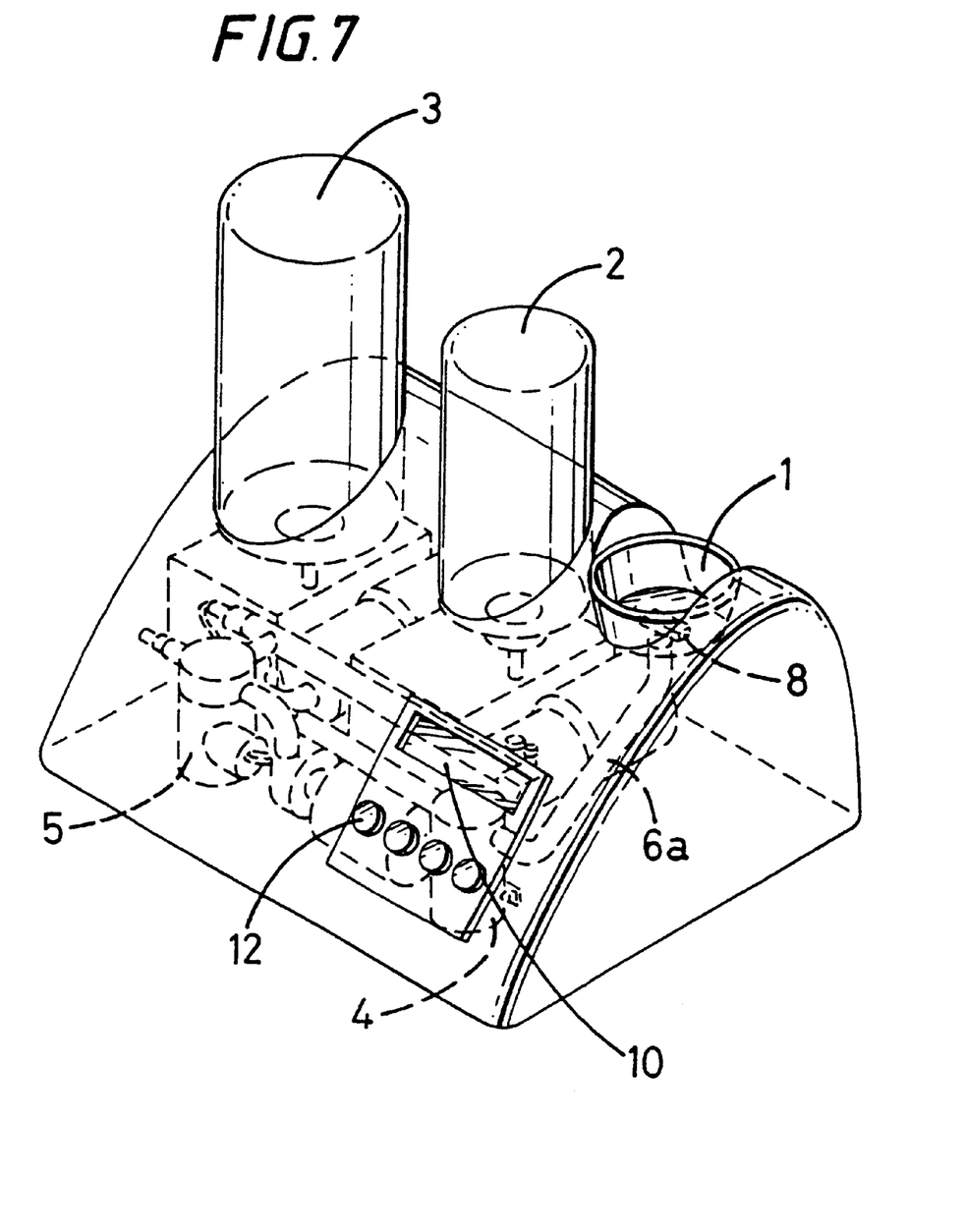
FIG. 7 is a perspective view of one embodiment of the apparatus according to the invention.

FIG. 7 shows a perspective view from above and one side of one embodiment of an apparatus according to the present invention.

One embodiment of apparatus according to the invention is shown diagrammatically in FIG. 6. The embodiment shown in FIG. 7 uses the same reference numerals as in FIG. 6 to identify functionally similar elements. As such, a separate description of the elements of FIG. 7 is omitted for brevity.

The apparatus comprises a titration vessel (1), a metering burette (not shown) for transferring a metered sample of coolant to the titration vessel, a pH electrode (9), a first reservoir (2) for acid reagent and a second reservoir (3) for a neutralizing agent, for neutralizing titrated samples after testing. A first metering pump (4) is provided for transferring metered additions of reagent acid from the first reservoir (2) to the titration vessel (1), by way of tubes (6, 6a). A second metering pump (5) is provided for transferring neutralizing agent from the second reservoir (3) to the titration vessel (1) by way of tubes (7, 7a), after the pH and any other measurements have been carried out. Means such as a magnetic stirrer (8) are provided in order to obtain good mixing of the test solution. If desired, another mixing device can be employed instead of the magnetic stirrer, such as a mixer or homogenizer to mix, stir or otherwise agitate the test solution.

A pH electrode (9) and optionally a refractometric probe (14) are provided for determining the pH and refractive index of the contents of the titration vessel (1). Electrode (9) and probe (14) are connected to a control unit (11) containing electronics including a start button (12), an analog signal treatment device (13), an analog to digital converter (20), and a microcontroller, or other type of computer or processor (30), with program software to treat the signals from electrode (9), to and from the metering pumps, and to an alphanumerical display (10) to show the results and test comments. Display (10) can be, for example, a liquid crystal display (LCD). Optionally the electronics also contain means for signal treatment to and from the refractometric probe (14), and software for signal processing of pH reading and determination of the freezing point based on a refractometric measurement, indicating the content of freezing point depressant. The display (10) can provide customized messages according to the results of the test.

Means are also provided in terms of software and standard solutions to calibrate the pH measurement and optionally the measurement of refractive index.

Titration Procedure

The following titration procedure is carried out in accordance with one embodiment of the invention on coolants in order to determine possible contamination with traditional corrosion inhibitors and the amount of carboxylate inhibitors present in a coolant sample:

1. A fixed volume, for example 25 ml of coolant, is taken out of an engine, radiator or expansion vessel of the cooling or heat-exchange system with a fixed metering pipette, and transferred to the titration vessel (1), e.g. with a syringe.
2. The calibrated pH-electrode (9) is brought into the titration vessel and acid reagent is pumped into the vessel through polytetrafluoroethylene (PTFE) tubes (6, 6a) connected to the first reservoir (2) containing hydrogen chloride solution at a fixed concentration (for example 2N HCl).
3. The start button (12) is activated to begin the measuring process. The liquid is stirred for instance by a magnetic stirrer (8).
4. A wait cycle, e.g. of 20 seconds, starts for stabilizing purposes. The pH of the test solution is recorded in the memory of the controller. If the initial pH is below a limited value acceptable for the coolant, the process stops and a warning message is displayed on the LCD. Optionally, the initial pH is shown on the LCD screen.
5. If the pH is above the limited value accepted for the coolant, the microcontroller generates a pulsed signal to the first metering pump (4) and acidic reagent is dosed at an exact rate into the titration vessel (1). A typical addition rate is 1 cm$^3$/min.
6. The microcontroller keeps track of the measured pH and the dosed amount of reagent. If the pH reaches the first equilibrium point, corresponding to a pH of 7.0, the quantity of reagent acid that has been added is stored and used to calculate the "Contamination level". This contamination level is displayed on the LCD screen. If this level exceeds a limit value which is unacceptable for further use of the coolant (contamination limit), the process is stopped and a warning message is displayed.
7. If this contamination limit is not reached, the system continues and starts counting the amount of acid reagent dosed, and stores it in a second memory. The process continues until the pH reaches the second equilibrium point at pH 3. At this point the microcontroller stops the activating pulse signal to the metering pump (4). The recorded quantity of reagent dosed between the contamination point and the inhibitor level point is used to calculate the actual carboxylate corrosion inhibitor content. This value (in % reading) is displayed on the LCD screen.
8. The microcontroller then starts the generation of an activating pulse signal to the second metering pump (5), and a controlled amount of caustic waste treatment fluid is pumped from the second reservoir (3) through tubes (7,7a), which may also be formed from PTFE, into the titration vessel (1). This continues until the solution reaches a fixed pH value. The test fluid can then be removed and disposed of, together with normal coolant waste.

The microcontroller can, for example, be a BS2-IC model made by Parallax, Inc. The pumps can, for example, be MLP-200 and/or MLP-50 models made by Tagasago Electric, Inc.

According to an optional preferred embodiment of the invention, the content of freezing point depressant is measured at step 4. This can be done by means of refractometric probe (14). This probe may consist of a prism made of material with high refractive index (for instance flint glass with refractive index n=1.88), a near infrared light emitting diode (LED) and a radiation detector (e.g. a phototransistor or photodiode). Means are provided to reduce the influence of incident radiation (e.g. a near infrared transmitting filter on the detection side). A pulse technique is used to reduce aging of emitters and detectors. Using this pulse technique, dark current and incident light compensation makes the measurements more reproducible then conventional refractometric techniques. The amount of infrared radiation internally reflected within the prism will be a function of the refractive index of the test solution in which the prism is immersed. The microcontroller correlates the measured refractive index for the used medium (for instance an aqueous solution of ethylene glycol). The freezing point is then displayed on display (10).

Figure 5:
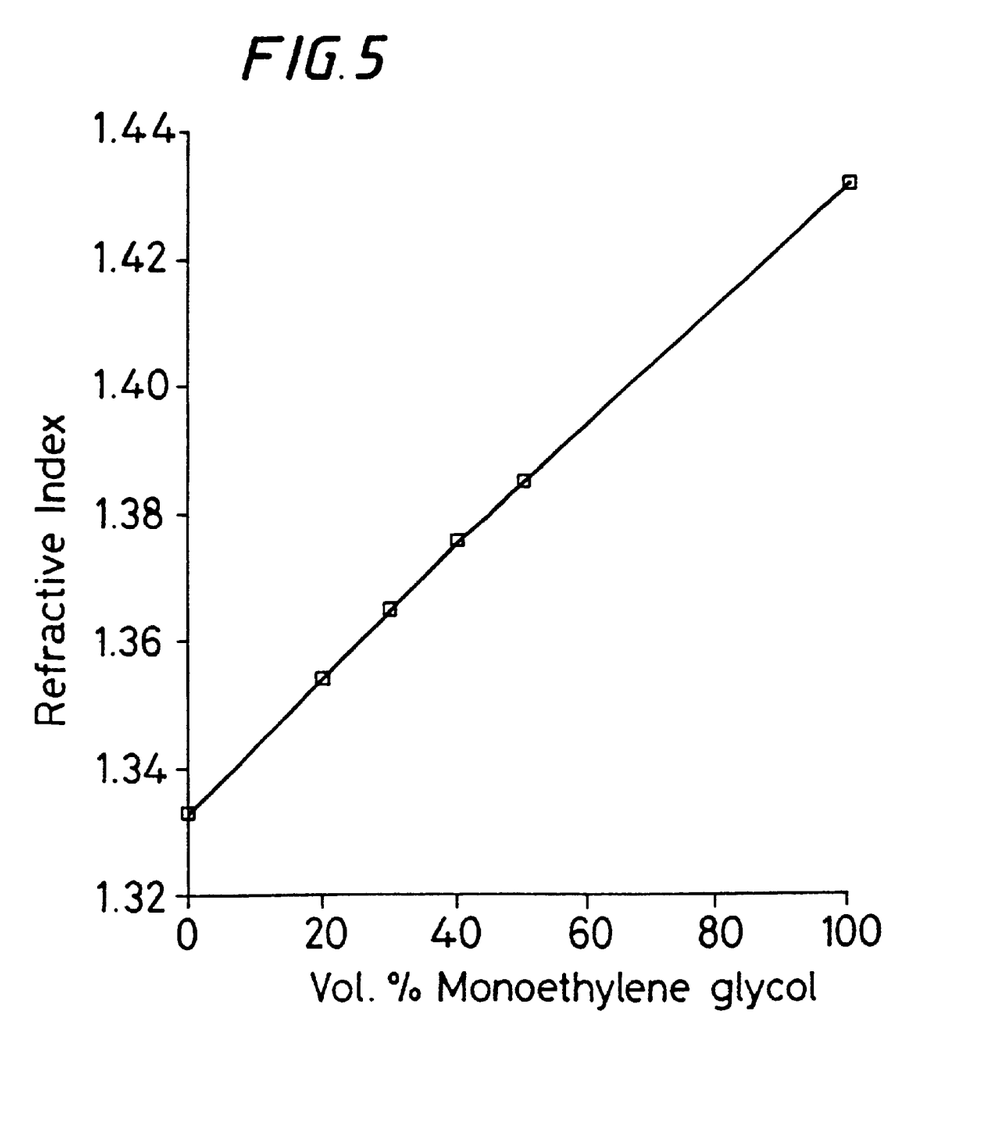
FIG. 5 shows a graph of the refractive index of systems containing different percentages (Vol. %) of monoethylene glycol.

FIG. 5 shows the results of measuring the percentage of monoethylene glycol by the refractive index methodology described above.

The apparatus can be easily modified to calculate and display the contamination levels and carboxylate contents for coolants other than XLC and AFC. Since this measurement is virtually independent of the base fluid, it can be used in aqueous glycol-free solutions or in mixtures of water and glycol and/or other freezing point depressants. Accordingly, the present invention is not limited to any particular coolant, heat-exchange fluid, or base fluid.

What is claimed is:

1. An instrument for quantifying the content of carboxylic acid-based corrosion inhibitors, contaminants, and glycol to water ratio in a sample of a predetermined amount of coolant or heat exchange fluid, comprising:
    (a) an acid titration means for adding an acidic reagent to the sample and measuring a pH of the sample, wherein said acid titration means includes:
        a means for measuring a pH of the sample,
        a means for recording a quantity of said acidic reagent added to the sample upon a first substantial drop in said pH, and
        a means for recording a quantity of said acidic reagent added to the sample upon a second substantial drop in said pH;
    (b) a means for determining a quantity of a contaminant based on said quantity of said acidic reagent added to the sample upon said first substantial drop in said pH;

(c) a means for determining a quantity of carboxylic acid-based corrosion inhibitors based on an amount of acidic reagent added between said first substantial drop in pH and said second substantial drop in pH;

(d) a means for determining a ratio of glycol to water in the sample, wherein said means comprises a determination of a refractive index of the sample;

(e) an indicator means for indicating said quantity of a contaminant;

(f) an indicator means for indicating said quantity of carboxylic acid-based corrosion inhibitors; and (g) an indicator means for indicating said ratio of glycol to water in the sample.

2. The instrument according to claim 1 further comprising a microprocessor for determining said quantity of a contaminant, said quantity of carboxylic acid-based corrosion inhibitors, and said ratio of glycol to water in the sample, and for indicating said quantity of a contaminant, said quantity of carboxylic acid-based corrosion inhibitors, and said ratio of glycol to water in the sample.

3. The instrument according to claim 1, wherein said means for measuring pH is automated.

4. The instrument according to claim 2, wherein said means for measuring pH is automated.

5. The instrument according to claim 1, wherein said refractive index of the sample is measured using a refractometric probe.

6. The instrument according to claim 1 further comprising an electrode to measure pH.

7. A method for quantifying the content of carboxylic acid-based corrosion inhibitors, contaminants, and glycol to water ratio in a sample of a predetermined amount of coolant or heat exchange fluid, comprising:

(a) adding an acidic reagent to the sample, (b) measuring a pH of the sample, (c) recording a quantity of said acidic reagent added to the sample upon a first substantial drop in said pH;

(d) recording a quantity of said acidic reagent added to the sample upon a second substantial drop in said pH;

(e) determining a quantity of a contaminant based on said quantity of said acidic reagent added to the sample upon said first substantial drop in said pH;

(f) determining a quantity of carboxylic acid-based corrosion inhibitors based on an amount of acidic reagent added between said first substantial drop in pH and said second substantial drop in pH, (g) measuring a refractive index of the sample, (h) determining a ratio of glycol to water in the sample based on the refractive index of the sample.

8. The method of claim 7, wherein said steps of determining said quantity of a contaminant, said quantity of carboxylic acid-based corrosion inhibitors, and said ratio of glycol to water in the sample, and indicating said quantity of a contaminant, said quantity of carboxylic acid-based corrosion inhibitors, and said ratio of glycol to water in the sample are performed on a microprocessor.

9. The method of claim 8, wherein said step of measuring pH is automated.

10. The method of claim 9, wherein said step of measuring pH is automated.

11. The method of claim 7, wherein said refractive index of the sample is measured using a refractometric probe.

12. The method of claim 7, wherein pH is measured using an electrode.

* * * * *